(12) United States Patent
Fey et al.

(10) Patent No.: US 8,587,785 B2
(45) Date of Patent: Nov. 19, 2013

(54) SAMPLE CHAMBER FOR MONITORING THE CONCENTRATION OF COMPONENTS OF ADDITIVES IN A PRINTING PROCESS LIQUID

(75) Inventors: Dirk Fey, Neewiller (FR); Gunther Krieg, Karlsruhe (DE)

(73) Assignee: Prof. Dr.-Ing. Gunther Krieg, Karlsruhe (DE)

( * ) Notice: Subject to any disclaimer, the term of this patent is extended or adjusted under 35 U.S.C. 154(b) by 0 days.

(21) Appl. No.: 13/464,105

(22) Filed: May 4, 2012

(65) Prior Publication Data

US 2012/0218553 A1 Aug. 30, 2012

Related U.S. Application Data (63) Continuation of application No. 11/336,810, filed on Jan. 23, 2006.

(30) Foreign Application Priority Data

Jan. 24, 2005 (DE) .......................... 10 2005 003 372

(51) Int. Cl.
  *G01N 21/00* (2006.01)
  *B41F 33/00* (2006.01)
(52) U.S. Cl.
  USPC ........................... 356/440; 356/246; 101/484
(58) Field of Classification Search
  USPC ................... 356/244, 246, 432–440; 101/484
  See application file for complete search history.

(56) References Cited

U.S. PATENT DOCUMENTS

| 2,017,867 | A |   | 10/1935 | Nantz |
|---|---|---|---|---|
| 3,999,867 | A | * | 12/1976 | Stabell .......................... 356/246 |
| 4,761,381 | A | * | 8/1988 | Blatt et al. .................... 436/165 |
| 4,804,267 | A | * | 2/1989 | Greenfield .................... 356/335 |
| 4,983,038 | A | * | 1/1991 | Ohki et al. .................... 356/246 |
| 5,726,751 | A | * | 3/1998 | Altendorf et al. ............. 356/246 |
| 6,188,474 | B1 | * | 2/2001 | Dussault et al. ............. 356/246 |
| 7,105,355 | B2 | * | 9/2006 | Kurabayashi et al. ........ 436/165 |
| 7,595,871 | B2 | * | 9/2009 | Weber ........................... 356/246 |
| 7,911,615 | B2 | * | 3/2011 | Martino et al. ............... 356/436 |
| 2004/0080744 | A1 | * | 4/2004 | Hobbs ........................... 356/246 |
| 2005/0061188 | A1 |   | 3/2005 | Krieg et al. |
| 2006/0087654 | A1 | * | 4/2006 | Wolf et al. ................... 356/436 |

FOREIGN PATENT DOCUMENTS

| DE | 41 06 313 |   | 9/1992 |
| DE | 19849847 | A | 5/2000 |
| DE | 103 33 625 |   | 2/2005 |
| JP | 04327940 | A | 11/1992 |
| JP | 2000 301698 |   | 10/2000 |
| JP | 2002 107290 |   | 4/2002 |
| JP | 2002 350233 |   | 12/2002 |

* cited by examiner

*Primary Examiner* — Hoa Pham
(74) *Attorney, Agent, or Firm* — Robert P. Michal; Lucas & Mercanti, LLP

(57) ABSTRACT

The invention concerns a sample chamber used for monitoring the concentrations of components of additives in a printing process liquid for maintaining predetermined desired concentrations of components of additives in a printing process liquid, wherein the actual concentrations of components are determined followed by redosing of measured components to a predetermined desired concentration.

8 Claims, 11 Drawing Sheets

SAMPLE CHAMBER FOR MONITORING THE CONCENTRATION OF COMPONENTS OF ADDITIVES IN A PRINTING PROCESS LIQUID

CROSS-REFERENCE TO RELATED APPLICATIONS

This is a Continuation application under 37 CFR 1.53(b) of pending application Ser. No. 11/336,810 filed Jan. 23, 2006, which in turn claims the benefit under 35 USC 119 of German Patent Application Serial No. 10 2005 003 372.5 filed Jan. 24, 2005, the entire contents of each of which is incorporated herein by reference.

FIELD OF THE INVENTION

The invention concerns a sample chamber for monitoring the concentrations of components of additives in a printing process liquid.

BACKGROUND OF THE INVENTION

In offset printing machines, the printing plate is wet with an aqueous liquid using a so-called dampening system, such that image areas accept the ink in a subsequent processing step, whereas the image-free areas repel the ink. In addition to water, the aqueous liquid often contains an alcohol mixture, in most cases isopropanol, as well as a chemical mixture of up to approximately twenty substances (referred to below as an additive). The additive is dosed in concentrations of between 1 and 8 vol. % and the alcohol is added in concentrations of between 0.5 and 20 vol. %. The concentration of water is therefore between 72 and 98.5 vol. %. If optimized additives are used, alcohol is sometimes completely omitted. In this case, the additive is also called an alcohol substitute. The optimized additive either completely or partially assumes the function of the isopropanol. Additives substantially contain the following substance groups:

- surface-active substances such as higher alcohols and tensides which reduce, in particular, the dynamic surface tension, and are used, possibly partially, as an isopropanol substitute,
- buffers, in particular phosphate and citrate buffers which maintain the pH value of the dampening solution at a constant value in a range between 4.8 and 5.3,
- wetting agents such as e.g. glycerine which make the printing plates hydrophilic,
- antioxidants as corrosion protection, glycols and glycol ether which act as solubilizers and keep the above-mentioned substance groups in the aqueous solution, and
- substances having a germ-killing effect.

One major problem in offset printing is the insufficient up-time of the very expensive printing machine, which is typically only approximately 80% and is therefore characterized by long down-times. One could e.g. save approximately 35,000.00 Euros per year if the pure productive time per day of a so-called 64 page rotary offset printing line could merely be increased by an average of two minutes. New, intensive practical examinations have clearly shown that the insufficient up-time of offset printing machines is essentially due to the undefined, unknown physical and chemical composition of the process liquid which, to date, cannot be measured and therefore cannot be regulated. These experiments showed, in a particular and in a paradoxical manner, that even if a predetermined volumetric mixture of the water and additive components is exactly realized, e.g. through precise control of two dosing pumps injecting e.g. volumes of 97 vol % water and 3 vol % additive into the process liquid, a much lower value is actually present in the process liquid circuit, e.g. 0.8 vol % of additive. Even more surprising, analyses have shown that the original percentage composition of the individual components of the additive in the dampening solution circuit do not correspond to the originally targeted composition which was injected by the dosing pumps through controlled feeding. Processes take place ("cannibalistic effects"), with which the components of the additive are consumed during the printing process to a greater or lesser degree despite the fact that they are added periodically in accordance with targeted concentration proportions. Current, conventional offset printing technology of feeding the additive concentrate in the form of one single chemical mixture which contains all required chemical components with precisely predetermined concentrations and whose composition depends on the application of pressure, i.e. roller offset, sheet-fed offset or newspaper printing and on the type of machine, paper, ink, in the dampening solution circuit of a printing machine, is an inadequate procedure which does not meet modern requirements for high up-time in the offset process. Although these disadvantages can be compensated for to a certain degree in printing with alcohol through the addition of higher concentrations of isopropanol, as is current practice, this method cannot be regarded as a technical solution for the future, since isopropanol, being a solvent and volatile component (VOC=volatile organic compound), is prohibited in offset printing in many US states, subject to strict laws for emission reduction in Europe, and even fined in Switzerland with a penalty tax, the so-called "Lenkungsabgabe", which is detrimental to the economics of the printing process. For political environmental reasons and, in particular, to protect the health of the printers at their workplace, isopropanol or other solvents must be substantially reduced or completely eliminated in future printing processes. The concentrations of alcohol in the dampening solution are currently generally between 6% and 20% and facilitate the use of so-called film dampening devices in roller and sheet-fed offset printing. In accordance with prior art, the film dampening devices comprise several rollers which are coated with rubber mixtures and/or metals and which are rotated together in contact with each other under slight pressure to transport the dampening solution, in the form of a film of adjustable film thickness, to the printing plate. This transport process is facilitated by the addition of isopropanol due to the reduction of surface tension of the liquid film caused thereby. In addition to conventional film dampening devices, contact-free operating systems, in particular, spray dampening devices operating with nozzles, or dampening devices comprising rollers jacketed with plush are also used. In these cases, the dampening means is transported without continuous liquid film, and use of alcohol may therefore be omitted. The new inventive method is also of great importance for conventional designs, since it permits optimum composition of chemicals in the dampening solution.

To meet the legal constraints regarding the ban of isopropanol, other solvents have been marketed, in particular in the U.S.A. This has not been the case in Europe, since this solution does not eliminate the use of solvents. Moreover, some of the other solvents are assumed to cause cancer or be detrimental to health and therefore do not constitute an alternative to alcohol.

A real alternative to alcohol are the so-called tensides which achieve comparable advantages with regard to the wetting properties of the dampening solution on the rollers of the dampening device. It must be noted, in particular, that tensides are not VOCs. Experience has shown that these positive tenside properties may be utilized only if the required targeted concentrations can be accurately met. In the currently used conventional alcohol-free methods, tensides produce undesired foams and emulsification of ink and dampening solution which reduces quality, such that, in many practical applications, printing without alcohol fails and must be replaced by printing with alcohol. This is further complicated by the fact that tensides in a chemical multi-component mixture often only dissolve with great difficulty, which requires the addition of solvents into the additive concentrate to prevent separation, i.e. deposit on the bottom of the additive container of the supplier. This difficulty is also easily solved by the inventive method, which provides the possibility of applying only those chemical substance components which are absolutely necessary for the printing process. Since the sheet speeds of modern printing machines are constantly increasing, increasingly precise measurement and dosing of the individual chemical components are required. The inventive method is therefore essential to printing without alcohol. This is supported by the fact that, with exactly the same printing machine, the composition of the individual components of the additive must be variable—depending on the printing orders i.e. on the paper, the particular inks required by the specific customer, the specially used rubber blanket, the roller coating, etc. This is only possible with the new method described herein. This is particularly true since there is no single conventional additive anywhere in the world which permits printing without alcohol under all conditions that occur in a printing machine. This explains why printing managers want to repeatedly test other additive formulations to realize their printing orders. Nevertheless, each chemical formulation is a compromise and is therefore optimum only for a limited range of printing orders. In total, the current conventional procedure is very expensive and renders printing without alcohol impossible in practice, despite the above-mentioned legal regulations in Europe.

Conventionally, dosing means are used for generating the process liquid by volumetrically mixing the two or three components through control under fixed predetermined conditions and introducing them into the liquid circuit of the printing machine in accordance with the respective consumption, i.e. in accordance with discharge of the liquid to the paper being printed. In addition to mixing stations, which are operated by hand, systems with conventional dosing pumps are also currently used. A severe disadvantage of these systems is that neither malfunctions of the mixing means nor changes in the physical and/or chemical composition, e.g. due to chemical reactions or absorption or desorption processes by the printing ink, paper, the pipe conduit or machine modules, can be defined. In particular, evaporation processes produce considerable concentration errors in these classical dosing methods. The sensors for detecting the electrical conductance which are currently used as sole control instruments are unsuitable for quantitative measurement of the concentration of the respective additive or substitute, due to the strong and varying soiling of the process liquid. Moreover, the important conducting chemical components of the additives which permit printing cannot be detected through conductance measurements, since these substances cannot be dissociated in water. The pH probe which has been introduced more or less as a standard in offset printing can at most be used as an indicator shortly before the functional collapse of the printing process, since the required strong chemical buffering of the process liquid e.g. using citric acid, prevents change of the pH value even for large variations in the chemical composition.

OBJECTS AND SUMMARY OF THE INVENTION

The object of the present invention is therefore the readjustment to the respective target values through continuous measurement and regulation of the composition of the dampening solution, i.e. through continuous redosing of the individual, differently decreasing chemical components or selected groups of components, to increase the up-time of the offset printing process to values of competing gravure printing, i.e. to approximately 90 to 95%.

This object is achieved in accordance with the invention with a method of the above-mentioned type in that spectroscopic methods are used for measuring the components. The invention also provides measuring means with at least one spectrometer to solve the above-mentioned object in a device of the above-mentioned kind.

In accordance with the invention, a method and a device are used in printing technology which, for the first time, continuously measure the concentrations of the individual components of the additive due to selective attenuation of electromagnetic radiation, and regulate these to predetermined optimum values, thereby preventing losses in process liquid as well as overdosing of individual components of the additive such that the printing process can be continuously carried out with high stability and availability at an optimum working point. The selectivity of the measurement and regulation of the additive can be maintained not only for alcohol-free printing, i.e. with substitutes, but also in printing with admixtures of alcohol, since the alcohol does not falsify measurement of concentrations of the individual components of the additive. This is of main inventive importance. In accordance with the invention, the selective measurement of concentrations of the individual components or of groups of different chemical compounds is coupled to a dosing system which removes the various components from various containers via a system comprising cycled valves and pumps, and guides them in a controlled manner to the dampening solution. This new method decisively optimizes offset printing with alcohol. Printing without alcohol is initially provided on a basis which permits long term processing, thereby meeting the economic boundary conditions. The fact that the new method permits individual, online adjustment of the dampening solution to the respective printing order, i.e. paper type, ink type, sheet speed and other fundamental interactions between the ink and dampening solution in the offset process, prevents generally known problems, such as e.g. inadmissible deposits on the rubber blanket, undesired ink decomposition in the dampening solution, detrimental chemical etching of the printing plates etc. In particular, the insufficient variation possibilities for the concentrations of the individual chemical components of ready-to-use additives can be arbitrarily extended by the new method. Repeated dampening solution exchange, in particular due to the above-mentioned search for better dampening solution additives, the associated printing process downtime of several hours, the corresponding negative consequences associated with the disposal of the previously used dampening solution, and the associated disadvantageous effects on the overall economics of the printing process, are avoided by the new method.

The invention permits qualitative, continuous measurement and regulation of the concentrations of the individual components of the respective additive or the substitute in a matrix of up to 20 chemical components without falsifying influence of other substances such as e.g. in particular alcohols, dirt, ink and paper particles, gas bubbles, salts from the paper and other impurities, as are typical for offset printing.

Moreover, in accordance with the invention, the individual components can be measured and regulated with an accuracy between 10 ppm and 3.0% depending on the substance, since the different chemical contents of a statically predetermined additive mixture are not consumed in proportion to the concentration and the mixture consequently changes during the printing process, since the inks, the paper and also other effects produce a more or less selective depletion of the individual components. The present invention completely compensates for the depletion effects, produced in particular during offset printing, irrespective of the customer order input into the printing machine. The present invention solves the above-stated objects, in particular, in that the individual chemical components are continuously measured by a spectrometer and are supplied, in a controlled manner, to the dampening agent circuit in the form of pure, raw materials and/or as partial mixtures of several components, generally mixed with water, such that they easily dissolve in the dampening solution and, in particular, form no separate phases. In this way, chemical formulations may also be used which separate in a predetermined additive concentrate and therefore would not have led to a homogeneous solution. In accordance with the invention, the attenuation of electromagnetic radiation during passage through the dampening solution is utilized for determining the concentration.

While components to be measured are generally detected in the infrared range, in a preferred embodiment, the components to be measured are detected in the ultraviolet range. It has turned out that an admissible alcohol portion in the printing process liquid has no disturbing effect on the determination of the additive concentration in the UV range.

It has also turned out that, as mentioned above, the concentration of the components in the process liquid generally changes differently, i.e. vanishes in different amounts, during the printing process. However, individual components substantially vary in the same percentage amounts. To simplify the method and the inventive device, in one preferred embodiment, only the actual concentration of a part of the measured components is determined through the spectroscopic measurement of components, wherein the device comprises a concentration determining unit, preferably including a computer, and structured in such a manner that merely the concentration of part of the components can be determined.

For the above-mentioned reason, a further preferred embodiment determines the actual concentration of at least one representative component of a subgroup of components which are depleted in identical amounts during the printing process, and the components of the subgroup are redosed together. This can be effected in different ways. The individual components may all be separate such that the dosing elements receive only one uniform dosing signal determined by the above-mentioned measurement for the mentioned subgroup of components. Alternatively, a subgroup of components of the additives may also be present in a dosing container in the form of a partial mixture and can be dosed as such on the basis of the dosing signal derived from the concentration determination of the representative component. Towards this end, the inventive device has a control means for redosing a subgroup of components on the basis of the determined concentration of at least one component of the subgroup.

The concentrations of a partial group of components may be depleted in a similar but not identical manner such that, under certain circumstances, it may not be reasonable to measure the actual concentration of a certain component as a representative measurement, rather to determine the concentrations of all components of the partial group or certain components of the partial group and to assign a weighted average of the depleted concentration or to first perform an individual comparison between the actual concentration and a target concentration of the individual components and subsequently determine an average value of the vanished amount for use as a control signal in redosing, in particular, of a mixture of the components of the above-mentioned partial group. Accordingly, a preferred embodiment of the invention provides that, for a partial group of components, the amount to be redosed of a mixture containing the components is determined from individual measurements of the components, and the partial group of components is redosed in the form of a mixture, wherein the device in accordance with the invention comprises means for performing individual measurements of the components to determine an amount to be redosed of a mixture containing a partial group of components, and for redosing the partial group of components in the form of a mixture.

The individual spectra of the components are determined from the measured overall spectrum using conventional mathematical methods, such as e.g. by the method of the least squares (PLS=partial least square algorithm). Samples of different individual components are recorded by a spectrometer for calibration purposes. A calibration function can be determined for each component and used during operation to determine the concentration loss of the respective components in a later measurement. A group concentration for groups of individual components or even the overall concentration of an additive consisting of several individual components can be determined therefrom, which, within the scope of the inventive method, can be redosed in total as such.

Alternatively thereto, the maximum of the sum of all partial spectra of all components can be detected as an actual value. In an advantageous embodiment, the integral of the detected sum spectrum is determined and further processed as a measure of the overall concentration of the additives.

In a preferred embodiment, the process liquid is guided through a flow channel for spectral analysis, in which the measuring process takes place to permit continuous measurement. In particular, electromagnetic radiation may thereby be guided through the process liquid in an direction orthogonal to the flow surface. Towards this end, the measuring means comprises at least one sample chamber for interaction between the process liquid and the electromagnetic radiation, wherein the sample chamber comprises a flow channel through which the process liquid is guided, and wherein the optical path of the electromagnetic radiation is orthogonal to the flow surface of the process liquid. In a preferred embodiment, the flow channel is formed to taper in the central area in the flow direction, thereby increasing the flow velocity and avoiding deposit of dirt in the sample chamber. In a highly preferred embodiment, the flow channel is formed as a Laval nozzle having a minimum nozzle cross-section of between 0.5 mm and 3 mm. In accordance with the invention, the absorption spectrum of the components to be measured in the process liquid can preferably be detected.

BRIEF DESCRIPTION OF THE DRAWINGS

The invention is described in detail below with reference to the figures.

FIG. 1b shows a difference spectrum of the two spectra of FIG. 1a;

FIG. 4b shows a perspective rear view of the inventive sample chamber of FIG. 4a;

FIG. 4d shows a section of the inventive sample chamber of FIG. 4a;

Figure 1A:
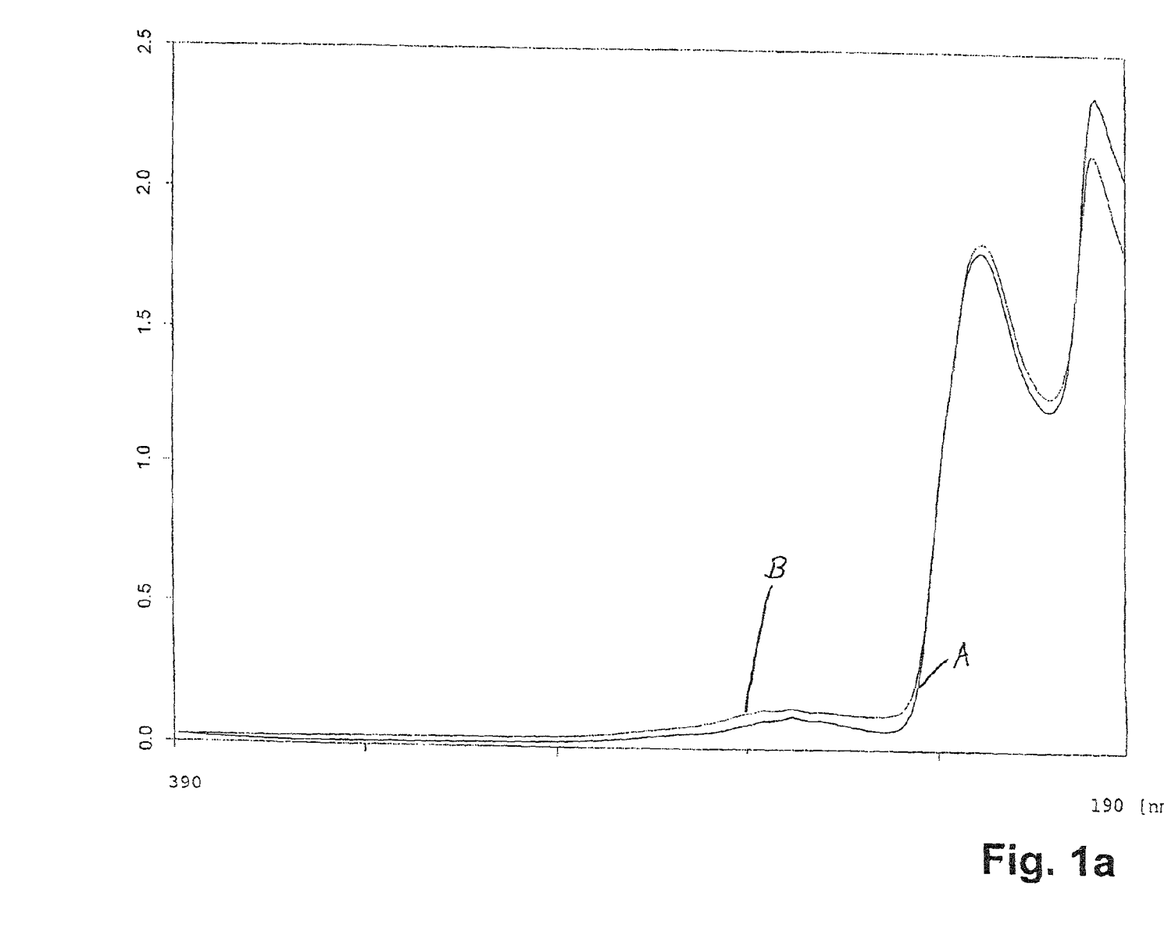
FIG. 1a shows UV spectra of a printing process liquid with fresh additive and after a certain operating period.
Figure 1B:
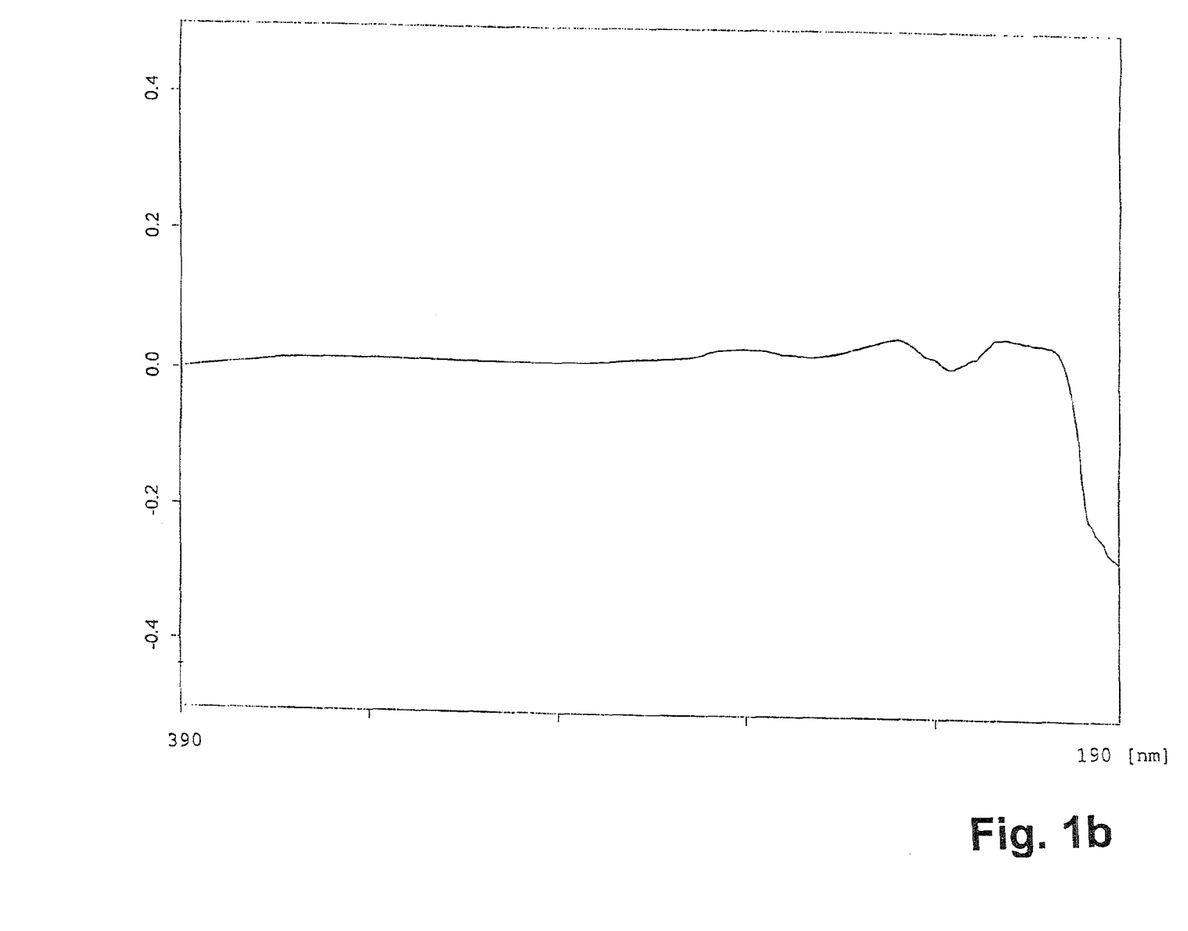

FIG. 1 shows, by way of example, a UV spectrum of a printing process liquid provided with fresh additive—spectrum A—and after a certain operating period—spectrum B. It is particularly obvious from FIG. 1b that both enrichment (spectrum over 0.0) as well as depletion (clear drop below 0.0 in the region close to 190 nm) are possible, depending on the component. This is due to the fact that individual components are discharged by the paper sheet to the process liquid during the printing process, while others can be absorbed from the process liquid by the paper sheet in different ways.

DETAILED DESCRIPTION OF THE INVENTION

The concentration of the individual components can be determined from the spectrum of FIG. 1a using conventional methods, such as the least squares method.

Figure 2:
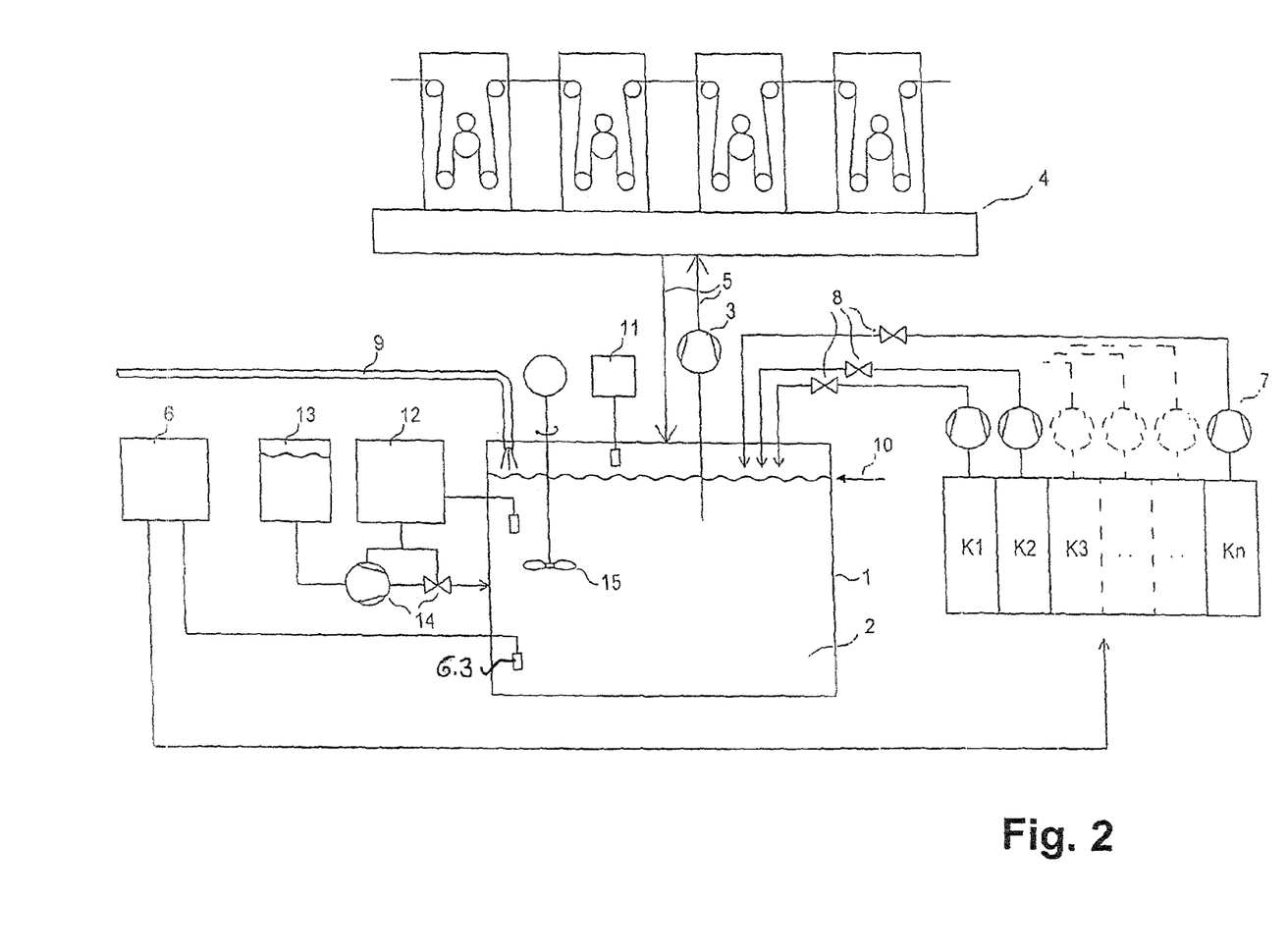
FIG. 2 shows the overall system consisting of measuring and regulation systems, printing machine and process liquid circuit, wherein the different chemical components/component groups are dosed directly by the measuring and regulation device.

In accordance with FIG. 2, the process liquid (2) contained in a tank (1) is circulated through the printing machine (4) and back to the tank (1) via circulating pumps (3) and pipe conduits (5). The respective individual chemical component concentrations of the additive are continuously measured by a measuring system (6). The predetermined chemical components K1, K2, K3, ... to Kn are fed into the process liquid (2) via pumps (7) and valves (8). The respectively required different desired concentrations of the chemical components K1 to Kn are assured in that the measuring system (6) continuously measures the actual concentrations and adds a corresponding amount of the respective component during regulation so that the actual value is equal to the specified, desired value. This ensures that the additive components, which are constantly consumed by the printing process or removed from the walls of the printing line through chemical reactions or physical absorption processes, are added to the process liquid (2) such that the actual values of the concentration of the additive are equal to the desired values defined by the printer and irrespective of the strength of the respective loss processes. The water loss in the process liquid (2) is compensated for via a pipe conduit (9), wherein the fill level (10) is kept constant using a level measuring and regulation system (11) in accordance with the ultrasound echolot principle or another conventional method. The concentration of the alcohol in the process liquid (2) (unless printing is effected without alcohol) is continuously measured using a further measuring and regulation means (12) which may also be integrated into the measuring system (6) in accordance with another design of the invention, and the alcohol loss caused substantially through evaporation is fed from a supply container (13) via a unit comprising a valve and dosing pump (14) such that the desired and actual values are always the same and the availability and quality of the printing process are also ensured for printing with alcohol. A stirring apparatus (15) is used to homogenize the process liquid.

Figure 3:
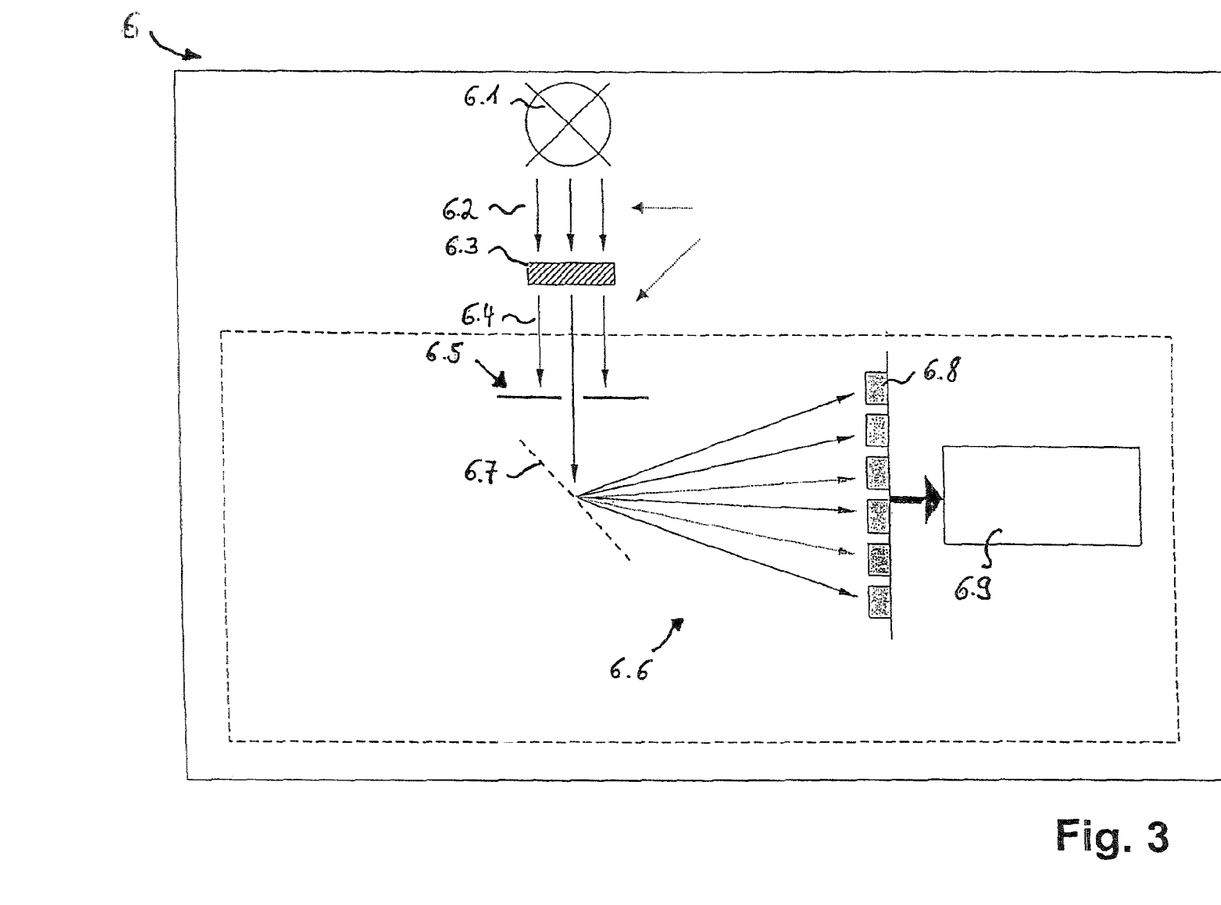
FIG. 3 shows a schematic view of the inventive measuring system.

FIG. 3 schematically shows an inventive measuring means (6). The inventive measuring means (6) initially comprises an illumination unit (6.1) in the form of a lamp which is an infrared lamp for IR spectroscopy and a UV lamp for UV spectroscopy. An optical path (6.2), e.g. in the form of an optical fiber which may also be suitable for guiding UV light in UV spectroscopy, extends from the illumination unit (6.1) to a sample chamber (6.3). This may be a sample chamber in the supply container (1) or a transparent tube piece in the line (5) between the supply container (1) and the printing machine. Another optical path (6.4), also in the form of optical fibers, extends from the sample chamber (6.3) to an optical configuration (6.5) which has, in particular, a slit. In the present embodiment, this is a grating spectrometer (6.6) comprising an optical grating (6.7) which is associated with a receiver configuration (6.8), in the present embodiment, a diode line. In principle, a prism spectrometer can also be used instead of a grating spectrometer.

The signals which were opto-electronically converted by the receiver unit (6.8) are supplied to an electrode unit (6.9). It includes, in addition to a computer, a regulation unit for comparing the actual and desired concentrations, a determining means for determining the amounts of the components to be redosed, and a control means for redosing the respective components.

The individual components of the additives in the process liquid are detected by the spectrometer, wherein the concentrations of the components can be determined through calibration using the obtained spectrum. These are also compared with the desired component concentrations in the electronics, whereupon, in case of differences, the amount of components to be redosed per unit time is determined followed by redosing of the corresponding components. This may be initially performed in that, as shown in the figures, the components are each contained in individual component containers (K1, K2, ...) from which the supply containers (1) are individually supplied in a manner described with reference to FIGS. 1 and 3 through 7.

Figure 4A:
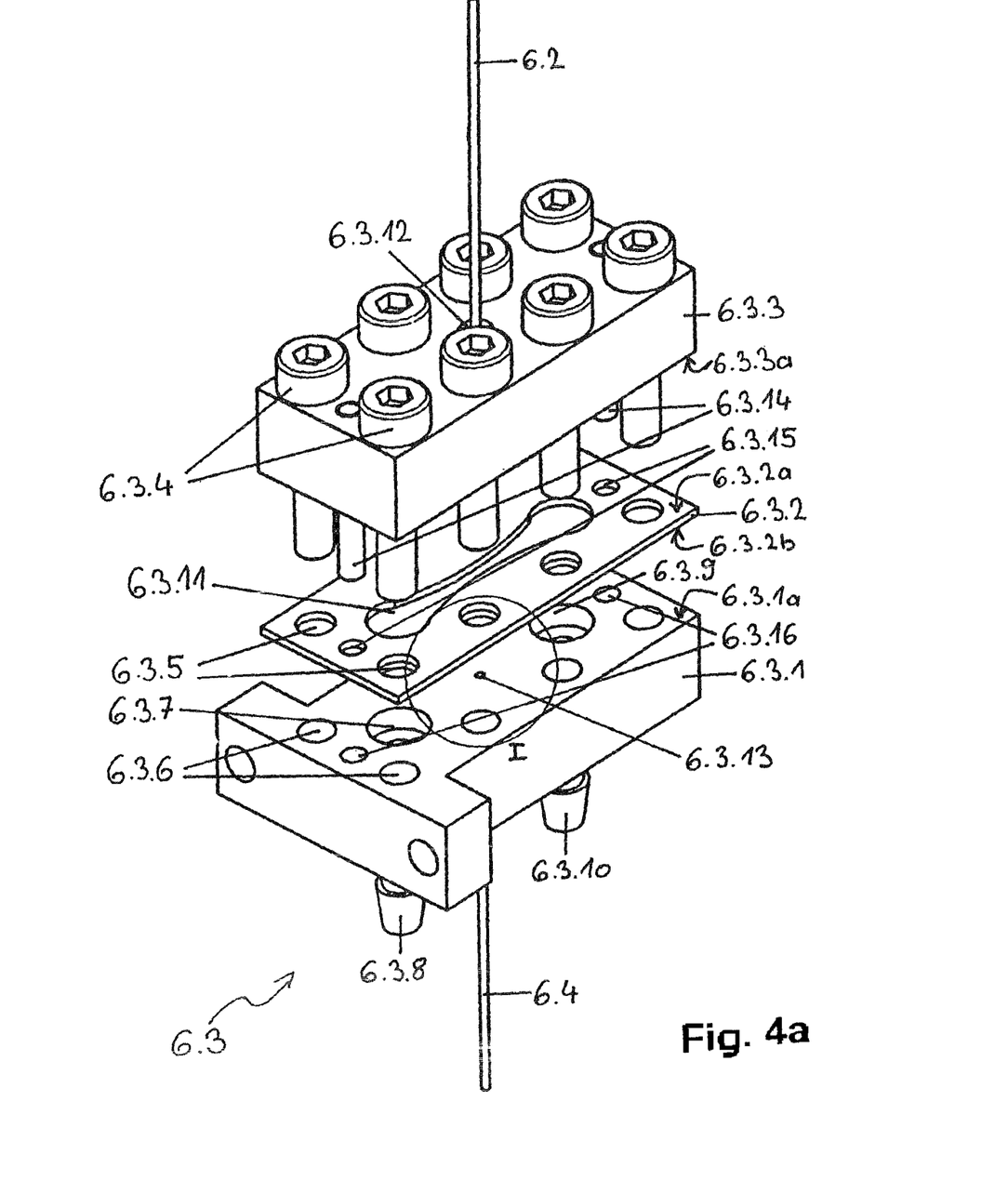
FIG. 4a shows a perspective front view of a preferred embodiment of the inventive sample chamber.

FIG. 4a shows a perspective exploded view of a preferred embodiment of the inventive sample chamber (6.3). It comprises a carrier element (6.3.1), an intermediate element (6.3.2) and a covering element (6.3.3). In the operative state of the sample chamber (6.3), these three components are rigidly screwed to each other using the threaded screws (6.3.4) provided on the covering element (6.3.3) for this purpose, and the associated threaded holes (6.3.6) provided in the carrier element (6.3.1) and the through holes (6.3.5) provided in the intermediate element (6.3.2) in such a manner that the inner surface (6.3.3a) of the covering element (6.3.3) and the inner surface (6.3.1a) of the carrier element (6.3.1) form a continuous liquid-tight connection with each outer surface (6.3.2a) and (6.3.2b) of the intermediate element (6.3.2). Towards this end, the intermediate element (6.3.2) is preferably formed from hard PVC, and the surfaces (6.3.1a) and (6.3.3a) as well as (6.3.2a) and (6.3.2b) contacting one another in pairs are preferably smoothed by polishing. To provide a continuous non-positive connection between the respective contacting surfaces, in a preferred embodiment, at least eight threaded screws (6.3.4) and at least eight associated threaded holes (6.3.6) are disposed in the carrier element (6.3.1) and at least eight associated through holes (6.3.5) are disposed in the intermediate element (6.3.2). Alternatively, the through holes (6.3.5) may also have a thread with positive fit corresponding to the threaded screws (6.3.4).

The carrier element (6.3.1) comprises an inlet bore (6.3.7) for supplying the process liquid (2) into the sample chamber (6.3), into which the process liquid (2) is supplied via a connecting element (6.3.8) having an inner tubular shape, e.g. by a connected tube line (not shown) or through direct supply. An outlet bore (6.3.9) has a further connecting element (6.3.10) disposed on the rear side for e.g. a hose pipe (not shown) in the carrier element (6.3.1) for discharging the supplied process liquid (2) after the measuring process.

The actual measuring chamber (6.3.11) of the sample chamber (6.3) is formed by the intermediate element (6.3.2), which, towards this end, has an opening (6.3.11) disposed on the end side at the level of the inlet bore (6.3.7) and outlet bore (6.3.9) respectively, and adjusted to the respective bore periphery (6.3.7) and (6.3.9), which serves as a flow channel between supplied and discharged process liquid (2). In a further development of the invention, the opening (6.3.11) is tapered in the central area. In a preferred embodiment, the width of the flow channel formed in this manner in the outlet area where the process liquid (2) exits the inlet bore (6.3.7) in the flow direction has an initial converging part with a minimum value in the center and an adjacent part that diverges until it enters into the outlet bore (6.3.9).

In accordance with the invention, the light beam is coupled and decoupled to the flow surfaces in an orthogonal direction. Towards this end, the covering element (6.3.3) and the carrier element (6.3.1) are each provided with a further bore (6.3.12) and (6.3.13) through each of which one optical guide (6.2) and (6.4) is disposed, flush with the inner surface (6.3.3*a*) and (6.3.1*a*), for feeding or extracting the measuring beam, such that it borders the upper or lower flow surface. The optical path of the measurement is formed by the thickness of the intermediate element (6.3.2) which is preferably in a range between 0.7 mm and 5 mm.

The bores (6.3.12) and (6.3.13) are preferably disposed in such a manner that the optical path of the measuring beam extends through the center of the flow channel, defined by the opening (6.3.11).

To exactly adjust the optical path during coupling or decoupling of the measuring beam by the optical fibers (6.2) and (6.4), the sample chamber (6.3) is produced in such a manner that the bores (6.3.12) and (6.3.13) are produced in one drilling process when the three components (6.3.1), (6.3.2) and (6.3.3) are screwed together. For fixing the optical path, the covering element (6.3.3) preferably comprises at least two fixing pins (6.3.14) which are each introduced into bores (6.3.15) and (6.3.16) disposed both in the intermediate element (6.3.2) and carrier element (6.3.1), wherein these bores (6.3.15) and (6.3.16) are also produced after the sample chamber (6.3) has been screwed together.

Figure 4B:
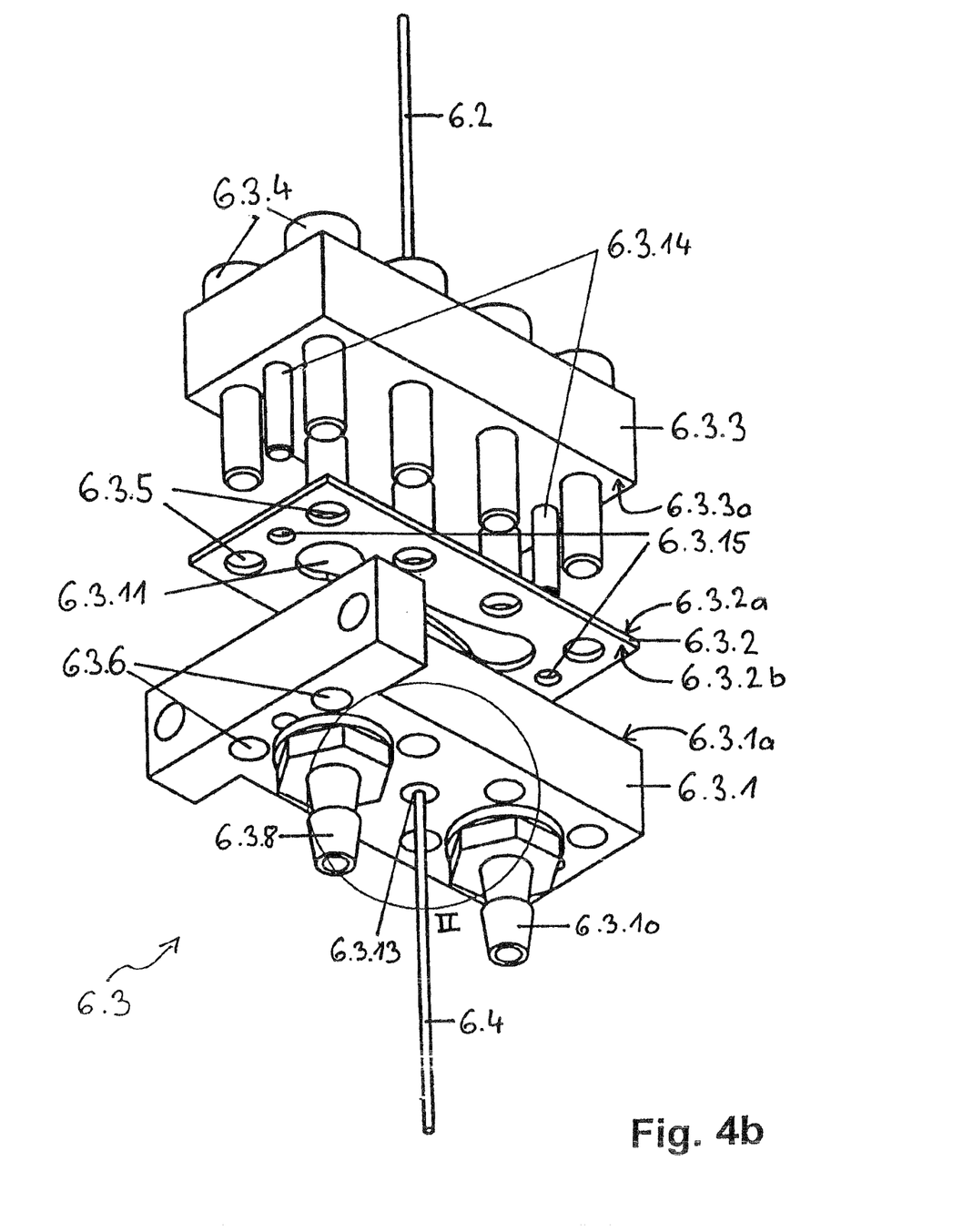
Figure 4C:
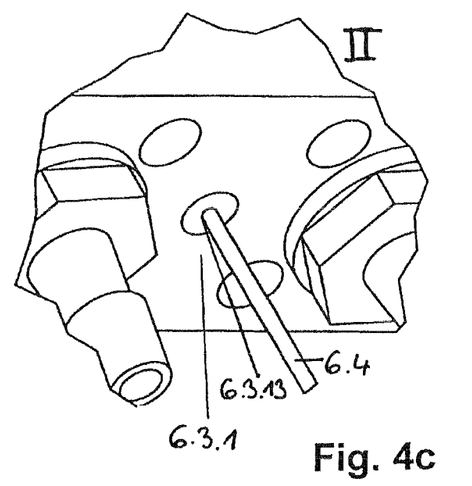
FIG. 4c shows a section of the inventive sample chamber of FIG. 4b.
Figure 4D:
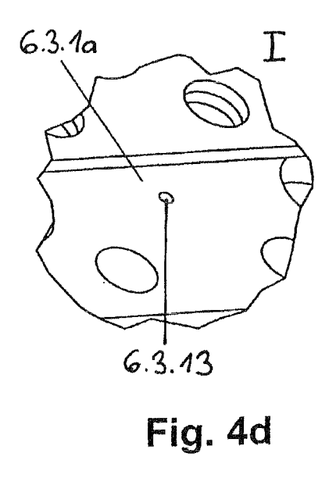
Figure 4E:
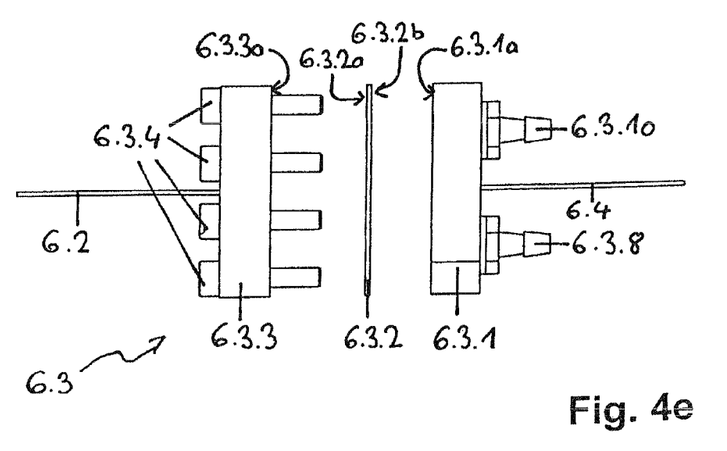
FIG. 4e shows a side view of the inventive sample chamber of FIGS. 4a and 4b.

FIGS. 4*b* and 4*e* further explain the individual components of the sample chamber (6.3) using perspective rear and side views, respectively. FIG. 4*c* and FIG. 4*d* show a detailed section (I) and (II) of FIG. 4*b* and FIG. 4*a*, to further explain fixing of the optical fiber (6.4) in the carrier element (6.3.1). After production of the bore (6.3.13), the optical fiber (6.4) is inserted into the bore until its end borders the inner surface (6.3.1*a*) or projects slightly beyond it. It is then fixed using a special adhesive to also seal the bore (6.3.13) in a liquid-proof manner. After the special adhesive has hardened, the optical fiber (6.4) is surface-ground, level with the inner surface (6.3.1*a*). An analogous method step is provided for fixing the optical fiber (6.2) in the covering element (6.3.3).

In an alternative manner, the above-described variations can be implemented to measure, detect and dose the individual components as well as to detect concentrations of a representative component for a subset of components and/or for adding a mixture of a subgroup of components to the supply containers.

Figure 5:
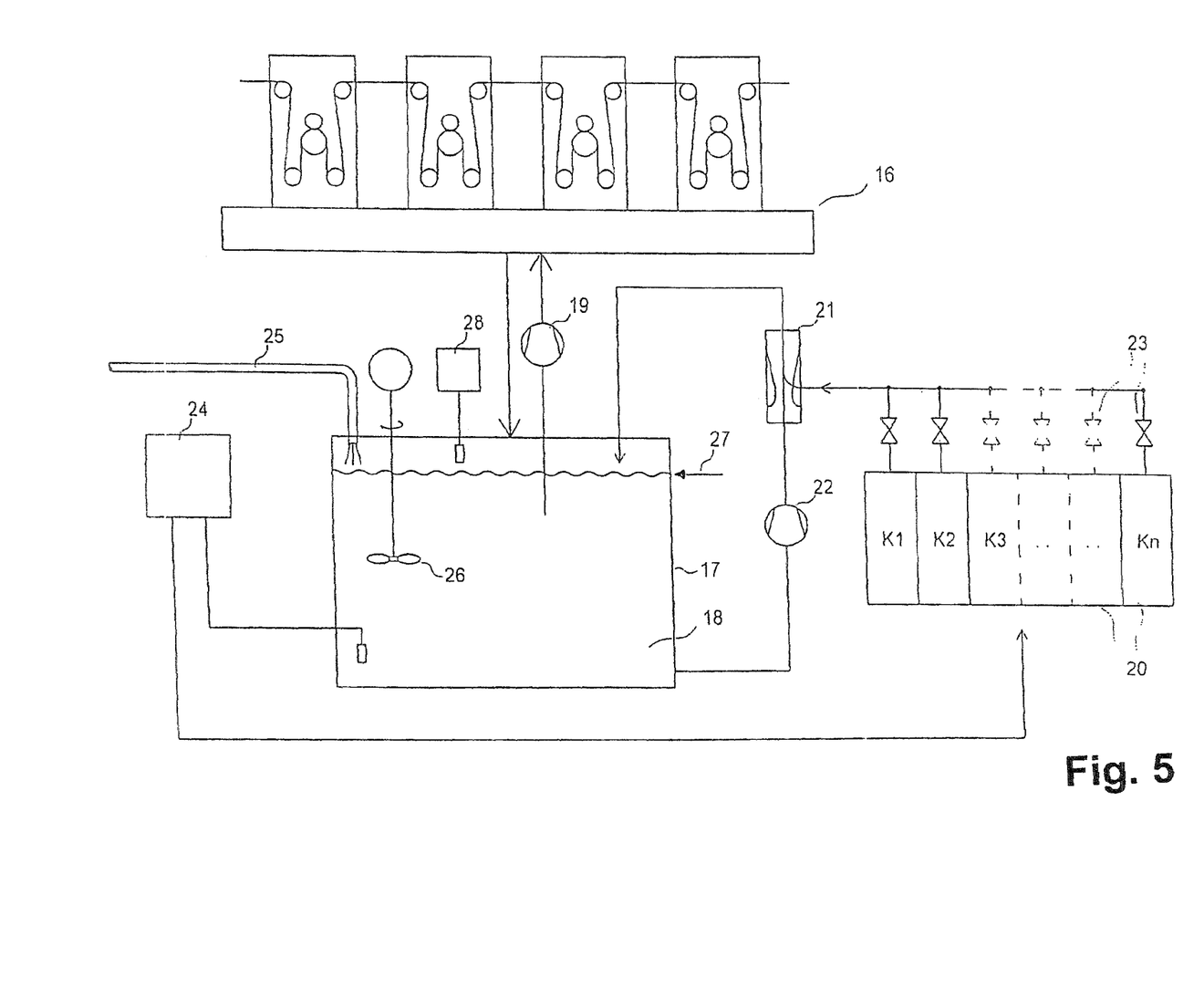
FIG. 5 shows an alternative embodiment of the invention, wherein dosing is effected using a Venturi nozzle.

FIG. 5 shows a sketch of the inventive arrangement which comprises a printing machine (16), a dampening solution tank (17), dampening solution (18) with circulation (19) and chemical components K1 through Kn (20) which are operated via a Venturi nozzle (21) and a pump (22), which suctions chemical components K1 through Kn via valves (23) and feeds them into the dampening solution (18), wherein the concentrations of the chemical components are measured via the measuring and regulation system (24). The supply (25) of water with automatic level regulation (via fill level control 28) and the stirring apparatus (26) correspond to the arrangements of FIG. 2.

Figure 6:
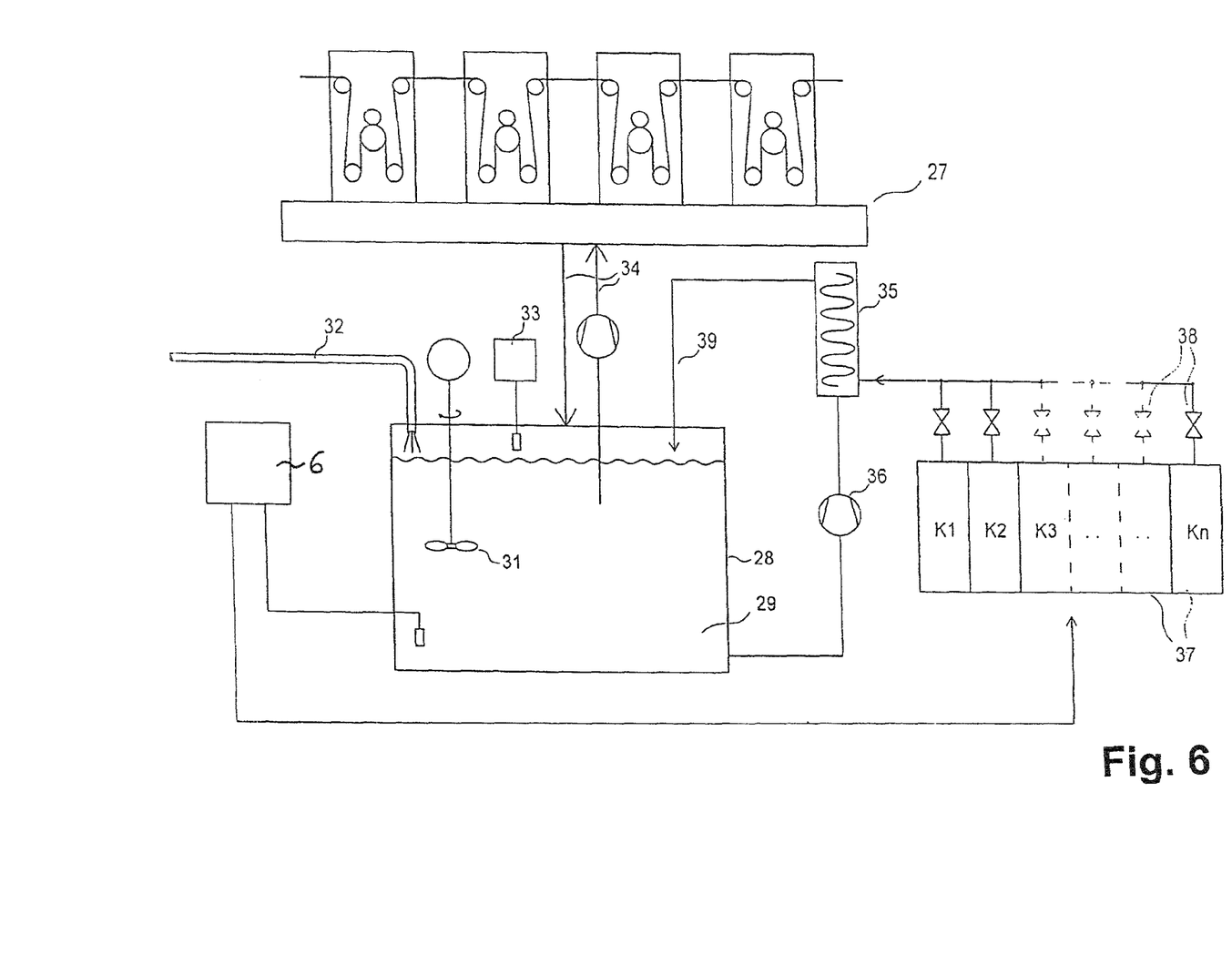
FIG. 6 shows an alternative embodiment of the invention which is characterized in that the individual chemical components are guided through a static mixer.

FIG. 6 shows an overall arrangement which consists of a printing machine (27), a dampening solution tank (28), dampening solution (29), a measuring and regulation system (6), a stirring apparatus (31), water supply (32) including fill level control (33), dampening solution circulation (34), and an additional static mixer (35). The dampening solution (29) which is passed through the circuit via the pump (36) is mixed, in the static mixer (35), with the chemical components K1 through Kn (37) which are supplied into the circuit (39) via the valves (38) such that both the measuring system (30) and the circuit (34) contain homogeneous liquid mixtures, such that the overall system of FIG. 6 provides optimum functioning.

Figure 7:
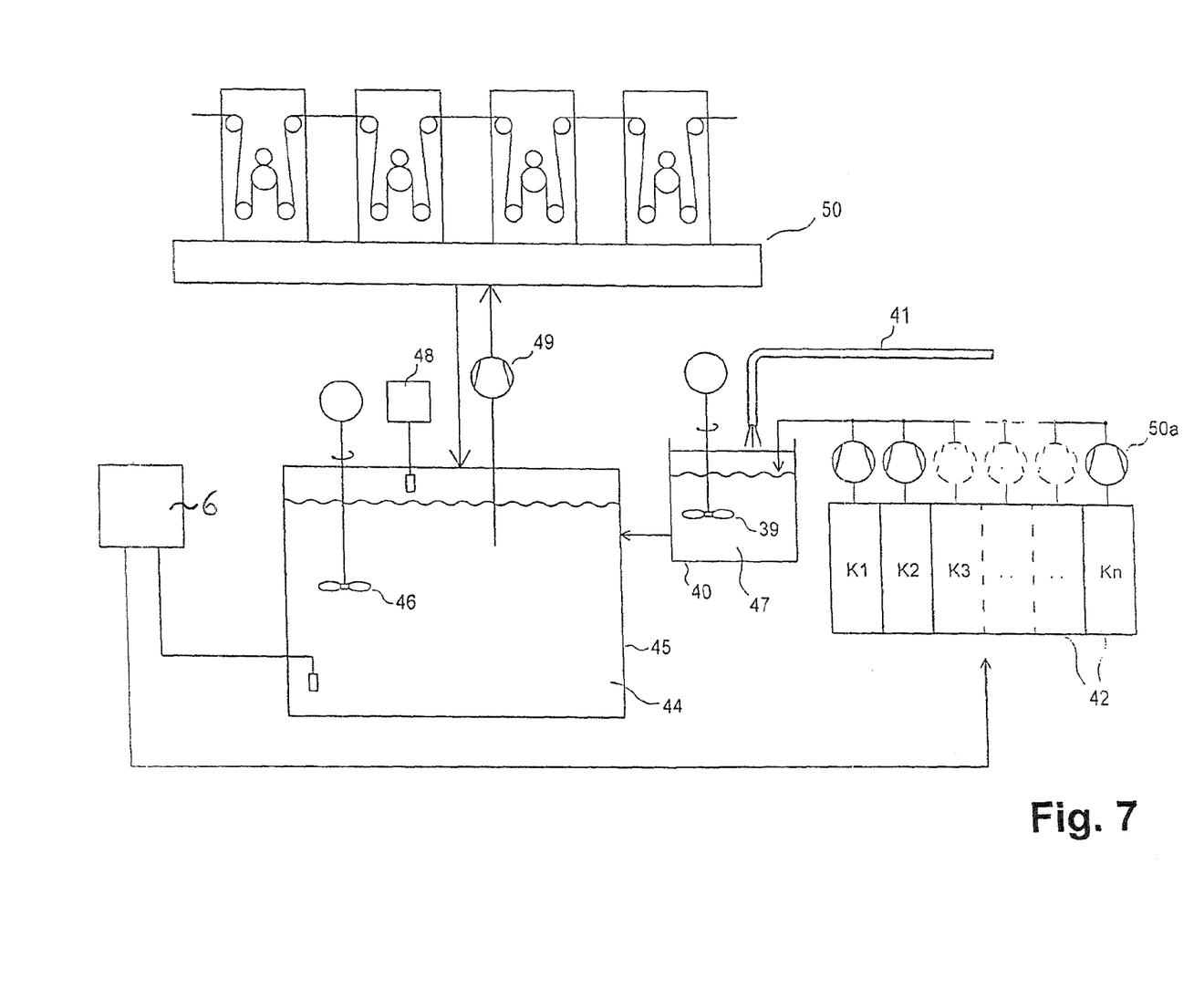
FIG. 7 shows a further system variant wherein previous mixing is effected in a separate container which is connected to the overall system, wherein the composition corresponds to the optimum mixing ratio.

FIG. 7 shows a version of the invention which differs from the previous figures and which is characterized by previous mixing of the chemical components K1 through Kn (42) with a water supply (41), in a mixing container (40) via pumps (50*a*). The arrangement considerably reduces the regulation process of the measuring system (6) to obtain the respective desired concentrations of the chemical components K1 through Kn (42), such that the composition of the dampening solution (44) in the dampening solution tank (45) always has the predetermined desired values, even over brief time intervals. Moreover, analogously to the stirring apparatus (46) in the dampening solution tank, a homogenizing means (39) is also used in the pre-mixing container (40). The homogenizing means (35) may also be a static mixer in accordance with FIG. 6. To prevent possible fill level problems during feeding of the pre-mixed liquid (47) into the dampening solution tank (45), the use of a sensor (48), preferably in accordance with the ultrasound echolot principle, is of great importance. Circulation of the dampening solution (44) to the printing machine (50) via the pump (49) is effected analogously to FIGS. 2 through 6.

Figure 8:
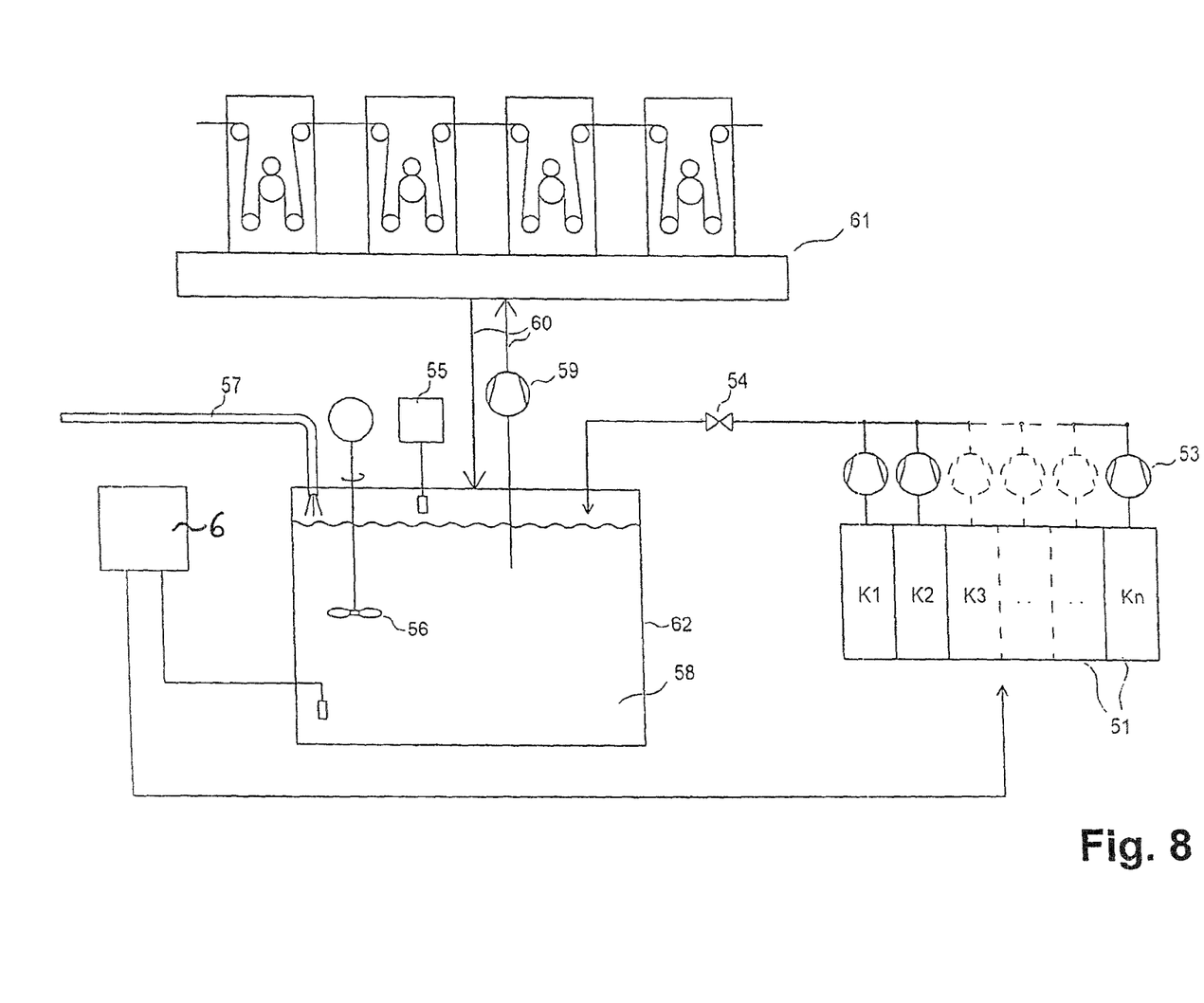
FIG. 8 shows a system, wherein the optimum composition is achieved via calibrated dosing pumps.

FIG. 8 shows the simplest variant in accordance with the invention, wherein the chemical components K1 through Kn (51) are added via a valve (54) using calibrated dosing pumps (53) regulated by the measuring system (6) in accordance with the respective desired value of the individual components. The fill level measurement (55) and the stirring apparatus (56) permit homogeneous mixing of the dampening solution (58) in combination with the water supply (57) which circulates in the circuit (60) between the printing machine (61) and dampening solution cooling device (62) via the circulating pump (59).

The invention claimed is:

1. A printing machine comprising a printing press liquid tank and a sample chamber disposed within the print liquid tank, the sample chamber monitoring the concentration of components of additives in a printing press liquid, comprising:

a carrier element having an outer surface, a single inlet bore opening to the outer surface, a single outlet bore opening to the same outer surface, and an inner surface on an opposite side of the carrier element from the outer surface;

a covering element having an outer surface, and an inner surface on an opposite side of the covering element from the outer surface;

an intermediate element having first and second outer surfaces, and a measuring chamber open to both the first and second outer surfaces, the intermediate element being disposed between the carrier element and the covering element such that the inner surface of the carrier element is proximate the second outer surface of the intermediate element and the inner surface of the covering element is proximate the first outer surface of the intermediate element, wherein the covering element further comprises an optical guide bore passing through the covering element such that an optical guide component passes therethrough from the covering element to the measuring chamber in the intermediate element, wherein the carrying element further comprises an optical guide bore passing through the carrying element such that another optical guide component passes therethrough from the carrying element to the measuring chamber in the intermediate element, and first and second connecting elements, the first connecting element being operatively fluidly coupled to the carrier element and providing a process liquid to the measuring chamber through the inlet bore, the second connecting element being operatively fluidly coupled to the carrier element to discharge the process liquid provided into the measuring chamber through the outlet bore, wherein the measuring chamber is configured such that the only inflow to the measuring chamber is process liquid that flows through the inlet bore of the of the carrying element and the only outflow from the measuring chamber is discharge of the process liquid through the outlet bore of the carrying element, wherein a flow channel is formed by the measuring chamber in the intermediate element, the inner surface of the carrying element and the inner surface of the covering element, the thickness of the flow channel defines an optical path length and the flow channel has in a downstream direction within a place of the intermediate element an initial converging part, leading to an increase of flow velocity of process liquid provided therethrough, and thereby preventing deposits of particles and dirt within the flow channel.

2. The printing machine of claim 1, wherein the carrier element further comprises an inlet bore operatively fluidly coupling the first connecting element to the measuring chamber and an outlet bore operatively fluidly coupling the second connecting element to the measuring chamber.

3. The printing machine of claim 1, wherein the optical guide traverses the measuring chamber.

4. The printing machine of claim 1, wherein the optical guide is operatively optically coupled to alight source such that a light beam is provided from the light source to the optical guide.

5. The printing machine of claim 1, wherein the carrier element, covering element, and intermediate element are coupled to form a liquid-tight connection.

6. The printing machine of claim 1, wherein the carrier element further comprises a plurality of threaded holes, the covering element further comprises a plurality of through holes passing from the outer surface to the inner surface of the covering element, and the intermediate element further comprises a plurality of through holes passing from the outer surface to the inner surface of the intermediate element.

7. The printing machine of claim 6, wherein the plurality of threaded holes of the carrier element are axially aligned with the plurality of holes of the covering element and the plurality of through holes of the intermediate element, further comprising a plurality or securing elements, the plurality of securing elements passing from the covering element through the intermediate element to the carrier element.

8. The printing machine of claim 1, wherein the optical guide directs electromagnetic radiation to penetrate the printing process liquid and move in an orthogonal direction with respect to the surface of the printing process liquid.

* * * * *

UNITED STATES PATENT AND TRADEMARK OFFICE
CERTIFICATE OF CORRECTION

| | | |
|---|---|---|
| PATENT NO. | : 8,587,785 B2 | Page 1 of 1 |
| APPLICATION NO. | : 13/464105 | |
| DATED | : November 19, 2013 | |
| INVENTOR(S) | : Dirk Fey et al. | |

It is certified that error appears in the above-identified patent and that said Letters Patent is hereby corrected as shown below:

In the Claims:

On column 12, line 20, please replace "alight" with --a light--, in order to have claim 4 (lines 20-23) read in its entirety as follows:

--4. The printing machine of claim 1, wherein the optical guide is operatively optically coupled to a light source such that a light beam is provided from the light source to the optical guide.--

Signed and Sealed this
Eighth Day of July, 2014

Michelle K. Lee
*Deputy Director of the United States Patent and Trademark Office*